United States Patent
Sorrentino et al.

(10) Patent No.: US 8,205,780 B2
(45) Date of Patent: Jun. 26, 2012

(54) APPARATUS FOR FORMING VARIABLE HEIGHT SURGICAL FASTENERS

(75) Inventors: Gregory Sorrentino, Wallingford, CT (US); Frank J Viola, Sandy Hook, CT (US); Scott Cunningham, Cheshire, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 194 days.

(21) Appl. No.: 12/529,576

(22) PCT Filed: Mar. 20, 2008

(86) PCT No.: PCT/US2008/057599
§ 371 (c)(1),
(2), (4) Date: Sep. 2, 2009

(87) PCT Pub. No.: WO2008/118728
PCT Pub. Date: Oct. 2, 2008

(65) Prior Publication Data
US 2010/0006620 A1    Jan. 14, 2010

Related U.S. Application Data

(60) Provisional application No. 60/919,381, filed on Mar. 22, 2007.

(51) Int. Cl.
*A61B 17/064* (2006.01)
(52) U.S. Cl. .................. 227/176.1; 227/175.1; 606/219
(58) Field of Classification Search .... 227/175.1–182.1; 606/131, 219
See application file for complete search history.

(56) References Cited

U.S. PATENT DOCUMENTS

| | | | |
|---|---|---|---|
| 3,499,591 A | 3/1970 | Green | |
| 3,771,526 A | 11/1973 | Rudie | |
| 4,319,576 A | 3/1982 | Rothfuss | |
| 4,429,695 A | 2/1984 | Green et al. | |
| 4,605,001 A * | 8/1986 | Rothfuss et al. | 227/178.1 |
| 4,608,981 A | 9/1986 | Rothfuss et al. | |
| 4,610,383 A | 9/1986 | Rothfuss et al. | |
| 4,633,874 A * | 1/1987 | Chow et al. | 227/176.1 |
| 4,741,336 A | 5/1988 | Failla et al. | |

(Continued)

FOREIGN PATENT DOCUMENTS
EP  0878169  11/1998
(Continued)

OTHER PUBLICATIONS

International Search Report for Int'l Appln. No. PCT/US2008/057599 dated Aug. 4, 2008.

*Primary Examiner* — Paul R Durand

(57) ABSTRACT

A surgical device for applying a plurality of surgical staples is provided. The device includes a staple fastening assembly attached to a surgical instrument. The staple fastening assembly includes a pair of cooperating jaws, a jaw operating mechanism, and a gap sensor. A staple magazine having a plurality of staples and an anvil member having a plurality of staple pockets are attached to the jaws. The staple magazine includes a staple crimping cam and a staple dimpling cam that are operatively coupled to the surgical instrument. The jaw operating mechanism is operatively connected to a drive assembly in the surgical instrument for moving the jaws for automatically setting a tissue gap between the cooperating jaws. The gap sensor cooperates with the jaw operating mechanism for controlling staple formation.

11 Claims, 6 Drawing Sheets

U.S. PATENT DOCUMENTS

| | | |
|---|---|---|
| 4,767,044 A | 8/1988 | Green |
| 4,809,695 A | 3/1989 | Gwathmey et al. |
| 4,848,637 A | 7/1989 | Pruitt |
| 4,930,503 A | 6/1990 | Pruitt |
| 4,941,623 A | 7/1990 | Pruitt |
| 4,978,049 A | 12/1990 | Green |
| 5,027,834 A | 7/1991 | Pruitt |
| 5,065,929 A | 11/1991 | Schulze et al. |
| 5,108,422 A | 4/1992 | Green et al. |
| 5,156,614 A | 10/1992 | Green et al. |
| 5,180,092 A | 1/1993 | Crainich |
| 5,201,746 A | 4/1993 | Shichman |
| 5,219,353 A | 6/1993 | Garvey, III et al. |
| 5,240,163 A | 8/1993 | Stein et al. |
| 5,282,829 A | 2/1994 | Hermes |
| 5,342,396 A | 8/1994 | Cook |
| 5,350,400 A | 9/1994 | Esposito et al. |
| 5,358,506 A * | 10/1994 | Green et al. ............... 606/151 |
| 5,397,324 A * | 3/1995 | Carroll et al. ............... 606/139 |
| 5,452,836 A | 9/1995 | Huitema et al. |
| 5,452,837 A | 9/1995 | Williamson, IV et al. |
| 5,480,089 A | 1/1996 | Blewett |
| 5,484,095 A | 1/1996 | Green et al. |
| 6,669,073 B2 | 1/1996 | Blewett |
| 5,497,931 A | 3/1996 | Nakamura |
| 5,501,693 A | 3/1996 | Gravener |
| 5,509,920 A | 4/1996 | Phillips et al. |
| 5,571,116 A | 11/1996 | Bolanos |
| 5,571,285 A | 11/1996 | Chow et al. |
| 5,634,926 A | 6/1997 | Jobe |
| 5,667,526 A | 9/1997 | Levin |
| 5,667,527 A | 9/1997 | Cook |
| 5,676,674 A | 10/1997 | Bolanos et al. |
| 5,697,542 A | 12/1997 | Knodel et al. |
| 5,709,680 A | 1/1998 | Yates et al. |
| 5,741,268 A | 4/1998 | Schutz |
| 5,810,822 A | 9/1998 | Mortier |
| 5,865,361 A | 2/1999 | Milliman et al. |
| 5,871,135 A | 2/1999 | Williamson, IV et al. |
| 5,915,616 A | 6/1999 | Viola et al. |
| 5,964,394 A | 10/1999 | Robertson |
| 6,083,242 A | 7/2000 | Cook |
| 6,202,914 B1 | 3/2001 | Geiste et al. |
| 6,325,810 B1 | 12/2001 | Hamilton et al. |
| 6,348,054 B1 | 2/2002 | Allen |
| 6,669,073 B2 | 12/2003 | Milliman et al. |
| 6,786,382 B1 | 9/2004 | Hoffman |
| 6,905,057 B2 | 6/2005 | Swayze et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 * | 10/2006 | Whitman ............... 227/180.1 |
| 7,455,676 B2 | 11/2008 | Holsten et al. |
| 2004/0004105 A1 | 1/2004 | Jankowski |
| 2004/0073222 A1 | 4/2004 | Koseki |
| 2004/0232195 A1 | 11/2004 | Shelton et al. |
| 2004/0232199 A1 | 11/2004 | Shelton et al. |
| 2004/0247415 A1 | 12/2004 | Mangone, Jr. |
| 2005/0006430 A1 | 1/2005 | Wales |
| 2005/0006431 A1 | 1/2005 | Shelton et al. |
| 2005/0006434 A1 | 1/2005 | Wales |
| 2005/0023324 A1 | 2/2005 | Doll et al. |
| 2005/0023325 A1 | 2/2005 | Gresham et al. |
| 2005/0070925 A1 | 3/2005 | Shelton, IV et al. |
| 2005/0070958 A1 | 3/2005 | Swayze et al. |
| 2005/0173490 A1 | 8/2005 | Shelton, IV |
| 2005/0178813 A1 | 8/2005 | Swayze et al. |
| 2005/0187576 A1 | 8/2005 | Whitman et al. |
| 2005/0263562 A1 | 12/2005 | Shelton, IV et al. |
| 2005/0267530 A1 | 12/2005 | Cummins |
| 2006/0000868 A1 | 1/2006 | Shelton, IV et al. |
| 2006/0015144 A1 | 1/2006 | Burbank et al. |
| 2006/0022014 A1 | 2/2006 | Shelton, IV et al. |
| 2006/0022015 A1 | 2/2006 | Shelton, IV et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton, IV et al. |
| 2006/0025816 A1 | 2/2006 | Shelton, IV |
| 2006/0025817 A1 | 2/2006 | Ortiz et al. |
| 2006/0039779 A1 | 2/2006 | Ring |
| 2006/0049230 A1 | 3/2006 | Shelton, IV et al. |
| 2006/0097026 A1 | 5/2006 | Shelton, IV |
| 2006/0124688 A1 | 6/2006 | Racenet et al. |
| 2006/0226196 A1 | 10/2006 | Hueil et al. |
| 2006/0273135 A1 * | 12/2006 | Beetel ............... 227/175.1 |
| 2007/0010838 A1 | 1/2007 | Shelton, IV et al. |
| 2007/0034666 A1 * | 2/2007 | Holsten et al. ............ 227/176.1 |
| 2007/0045379 A1 | 3/2007 | Shelton, IV |
| 2008/0210738 A1 * | 9/2008 | Shelton et al. ............ 227/176.1 |
| 2009/0206135 A1 * | 8/2009 | Hall et al. ............... 227/176.1 |

FOREIGN PATENT DOCUMENTS

| | | |
|---|---|---|
| EP | 0640315 | 12/1998 |
| EP | 1090592 | 4/2001 |
| EP | 1316290 | 6/2003 |
| EP | 1479346 | 11/2004 |
| EP | 1 728 473 A1 | 12/2006 |
| FR | 2838952 | 10/2003 |
| SU | 405234 | 9/1975 |
| SU | 1333319 | 8/1987 |
| SU | 1442191 | 12/1988 |
| SU | 1459659 | 2/1989 |
| WO | WO 90/05489 | 5/1990 |
| WO | WO 97/34533 | 9/1997 |
| WO | WO 03/094743 | 11/2003 |
| WO | WO 03/094747 | 11/2003 |

* cited by examiner

APPARATUS FOR FORMING VARIABLE HEIGHT SURGICAL FASTENERS

CROSS REFERENCE TO RELATED APPLICATIONS

This application is a National Stage Application of PCT/US2008/057599 filed DemARCH 20, 2008 under 35 USC §371(a), which claims priority of U.S. Provisional Patent Application Ser. No. 60/919,381 filed Mar. 22, 2007 the entire contents of which are hereby incorporated by reference.

BACKGROUND

1. Technical Field

The present disclosure relates to surgical fastener apparatus. More particularly, the present disclosure relates to apparatus for forming variable height surgical fasteners to body tissue in surgical procedures.

2. Background of Related Art

Surgical devices wherein tissue is first grasped or clamped between opposing jaw structure and then joined by means of surgical fasteners are well known in the art. In some instruments, a knife is provided to cut the tissue which has been joined by the fasteners. The fasteners are typically in the form of surgical staples.

Instruments for this purpose may include two elongated members which are respectively used to capture or clamp tissue. Typically, one of the members carries a cartridge which houses a plurality of staples arranged in at least two lateral rows while the other member includes an anvil which defines a surface for forming the staple legs as the fasteners are driven from the cartridge. Generally, the stapling operation is effected by a pusher which travels longitudinally through the cartridge carrying member, with the pusher acting upon the staples for sequentially ejecting them from the cartridge. A knife may travel with the pusher between the staple rows to longitudinally cut and/or open the stapled tissue between the rows of staples.

A later stapler disclosed in U.S. Pat. No. 3,499,591 applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples. Other examples of staplers are disclosed in U.S. Pat. Nos. 4,429,695, 5,065,929, and 5,156,614.

SUMMARY

The present disclosure is directed towards a staple fastening assembly for use with a surgical instrument to apply surgical staples. The staple fastening assembly includes cooperative first and second jaws, a jaw operating mechanism, and a staple driving assembly. One jaw is generally elongate and includes a staple magazine. The staple magazine may be fixedly attached or releasably attached to the jaw and includes a plurality of staples arranged in at least one row. A first tissue contacting surface is defined on one face of the staple magazine and includes a plurality of retention slots corresponding to the number of staples included in the staple magazine. It is contemplated that multiple rows of staples may be provided and arranged in columns. The retention slots may be longitudinally aligned or offset from one another. Each retention slot is configured and adapted for releasably receiving its respective staple. Each staple includes first and second substantially parallel legs connected by a backspan forming substantially right angles to each of the legs.

The second jaw is generally elongate and movable throughout a plurality of positions between an open position and a closed position. An anvil member is disposed on the second jaw and includes a second tissue contacting surface. The second tissue contacting surface includes a plurality of staple pockets wherein the number and arrangement of staple pockets corresponds to the number and arrangement of retention slots in the staple magazine. The second tissue contacting surface is oriented such that it is in juxtaposition with the first tissue contacting surface and defines a tissue gap therebetween.

Each staple pocket includes a pair of staple forming grooves for capturing the legs of each staple. The staple forming grooves are substantially symmetrical about an intermediate point and have opposing inclined surfaces. A substantially lemniscate channeling surface is formed about a perimeter of each staple pocket. Each staple forming groove urges one leg of each staple towards the other leg while maintaining lateral separation of the legs during and after staple formation.

The jaw operating mechanism is disposed in a housing that is attached to a proximal portion of the staple fastening assembly. The jaw operating mechanism includes a cam rotatably mounted to the housing, a cable, and a spring that are cooperatively coupled to one another. An approximating mechanism in the surgical instrument is operatively coupled to the jaw operating mechanism to cause proximal motion of the spring. Proximal movement of the spring is coupled to the cam via the cable. In one embodiment, the cam has an eccentric outer surface for maintaining contact between at least a portion of the outer surface of the cam and an outer surface of the second jaw. The cam may include an anti-reverse assembly (i.e. self-locking) to permit counter-clockwise rotation of the cam while inhibiting clockwise rotation of the cam. Configured thusly, counter-clockwise rotation of the eccentric cam continuously urges the second jaw towards the first jaw during proximal movement of the spring. The dimensions of the cam and the cable, as well as the dimensions and material selected for the spring, contribute towards the tissue capturing characteristics of the jaw operating mechanism. It is desirable for the jaws to capture and hold tissue in position while minimizing trauma to the tissue. Advantageously, the combination of the cam, the cable, and the spring allows for automatic adjustment of the tissue gap to accommodate different thicknesses of tissue during stapling operations.

BRIEF DESCRIPTION OF THE DRAWINGS

Embodiments of the presently disclosed surgical instrument are described herein with reference to the drawings, wherein.

DETAILED DESCRIPTION OF THE PREFERRED EMBODIMENTS

Figure 1:
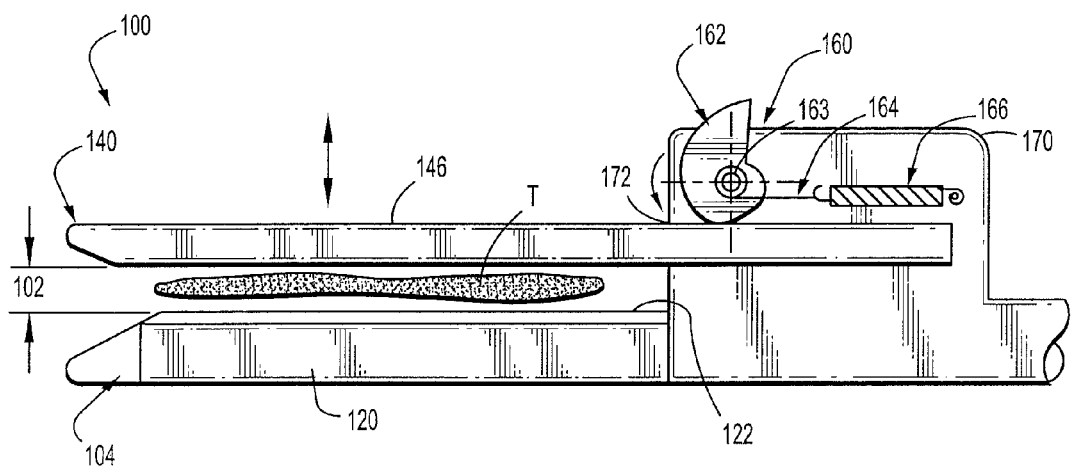
FIG. 1 is a side cross-sectional view of a staple fastening assembly in accordance with an embodiment of the present disclosure in an open position.

Embodiments of the presently disclosed surgical instrument will now be described in detail with reference to the drawings, in which like reference numerals designate identical or corresponding elements in each of the several views. As used herein, the term "distal" refers to that portion of the instrument, or component thereof which is further from the user while the term "proximal" refers to that portion of the instrument or component thereof which is closer to the user.

An example of a surgical stapling apparatus is disclosed in U.S. Pat. No. 5,480,089 to Blewett, currently owned by and assigned to United States Surgical, a division of Tyco Healthcare, the contents of which are hereby incorporated by reference in their entirety. Referring to FIG. 1, a staple fastening assembly, shown generally as 100, includes a fixed first jaw 104, a moveable second jaw 140, and a jaw operating mechanism 160. In one embodiment, staple fastening assembly 100 is adapted for use in connection with endoscopic or laparoscopic stapling instruments as are known in the art.

First jaw 104 includes a staple magazine 120 having a first tissue contacting surface 122. A plurality of retention slots 124 is included in staple magazine 120 where they are arranged in rows 126 on first tissue contacting surface 122 (see FIG. 4). Each row 126 generally extends along a longitudinal axis of first jaw 104. First tissue contacting surface 122 is generally elongate. Each retention slot 124 is configured for receiving a staple 110 and a staple ejector assembly. The staple ejector assembly includes a staple ejector 132, a dimpling rod 138 (see FIG. 5), a staple sled 134, and a rod sled 136. It is contemplated that staple magazine 120 may be removably attached to first jaw 104. In a configuration where staple magazine 120 is a removable structure, once its complement of staples 110 have been expended, it may be removed and a new staple magazine 120 is attached to first jaw 104. Each staple magazine 120 includes a full complement of staples 110 and at least one staple driving assembly 130 (shown in FIG. 5 and discussed in detail below).

Staple magazine 120 includes a plurality of longitudinal channels 128 (see FIGS. 3 and 4) that are adapted for slidably receiving staple sled 134 and rod sled 136. The number of channels 128 corresponds to the number of rows 126 of staples 110 included in staple magazine 120. In one embodiment, staple magazine 120 include at least two rows 126 of staples 110, although the procedure being performed, characteristics of the tissue to be fastened, and other considerations are factors in determining the number of rows 126, as well as the number of staples 110, included in each staple magazine 120. Each row 126 in the plurality of rows has an identical quantity of staples 110.

Figure 2:
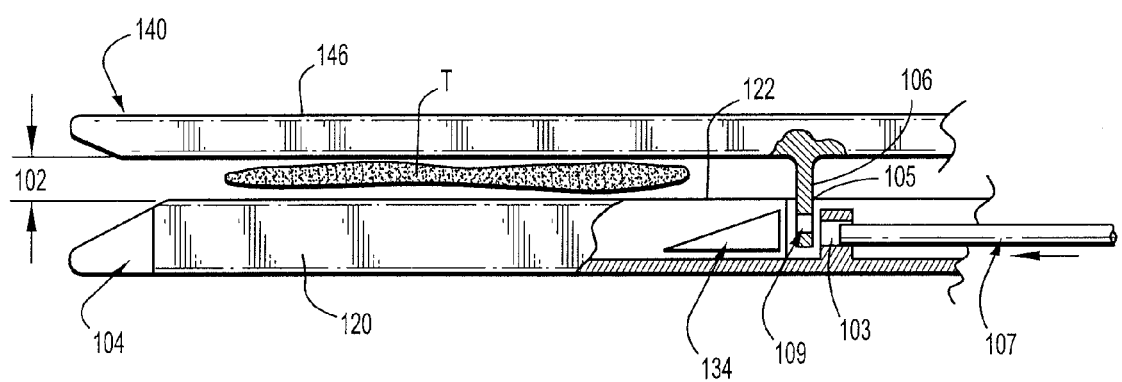
FIG. 2 is a side cross-sectional view of the staple fastening assembly of FIG. 1 in an intermediate position.
Figure 3:
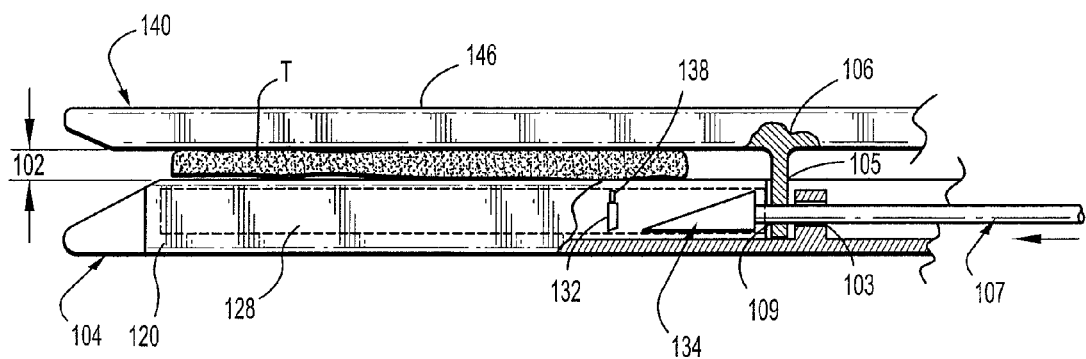
FIG. 3 is a side cross-sectional view of the staple fastening assembly of FIG. 1 in a closed position.

Referring now to FIGS. 5 and 8A-8C, in conjunction with FIGS. 1-3, staple driving assembly 130 is shown and it includes a staple ejector 132, staple sled 134, rod sled 136, and a dimpling rod 138. Each staple sled 134 is operatively coupled to a drive mechanism (not shown) of the surgical stapling instrument using structures that are known in the art. An example of such an instrument that includes a drive mechanism and an actuation mechanism is disclosed in U.S. Pat. No. 6,669,073 to Milliman et al., currently owned by and assigned to United States Surgical, a division of Tyco Healthcare, the contents of which are hereby incorporated by reference in their entirety. In embodiments that include a plurality of rows 126, staple sleds 134 are operatively coupled to the drive mechanism such that their longitudinal travel is synchronized for ejecting a column 127 of staples 110 (see FIG. 4) substantially simultaneously during an actuation sequence. Operation of the drive mechanism results in proximal and distal movement of the respective cams in response to actuation of the actuation mechanism.

Staple sled 134 is a generally elongate structure having a pair of inclined surfaces 135a, 135b oriented towards the distal end of staple magazine 120. Inclined surfaces 135a, 135b are laterally spaced apart to define a passage 135c therebetween. Passage 135c is substantially flat and dimensioned for slidably receiving rod sled 136. Rod sled 136 is a generally inclined structure having a substantially similar incline to that of staple sled 134. Further still, staple ejector 132 includes a pair of legs 132a, 132b that are laterally spaced apart and angled at their distal ends for readily engaging inclined surfaces 135a, 135b. A throughhole 132c is centrally disposed in body 132d of staple ejector 132 and is dimensioned for slidably receiving dimpling rod 138.

Upon actuation of the actuation mechanism, staple sled 134 is driven through staple magazine 120 in a generally distal direction by the drive mechanism. As it translates through staple magazine 120, staple sled 134 sequentially engages each staple ejector 132. Staple sled 134 and staple ejector 132 have engaging surfaces with complementary angles such that distal horizontal motion of staple sled 134 results in vertical motion of staple ejector 132 which, in turn, drives staple 110 in a generally vertical direction towards anvil member 142. During distal movement of staple sled 134, rod sled 136 remains stationary in a proximal region of the magazine. In instances where a staple height of less than about 2.5 mm is desirable, as determined by tissue gap 102, the actuation mechanism actuates the drive mechanism and drives rod sled 136 distally as will be discussed in detail hereinafter.

With reference to FIGS. 2 and 3, a gap sensor 106 is disposed in a proximal portion of staple fastening assembly 100. Gap sensor 106 is a generally elongate structure having a throughhole 109 disposed near one end. Further still, gap sensor 106 is fixedly attached to second jaw 140 and slidably received in an opening 105. A dimple window 103 is disposed near a proximal portion of first jaw 104 and is configured for slidably receiving a dimpling rod driver 107. Dimpling rod driver 107 is operatively coupled to the actuation mechanism and engages staple dimpling cam 136 when dimple window 103 is aligned with dimpling rod driver 107. Gap sensor 106 is configured and dimensioned such that dimpling window 103 is aligned with dimpling rod driver 107 only when tissue gap 102 indicates that a staple height of less than about 2.5 mm is desired.

In an embodiment having a staple height of less than about 2.5 mm, staple sled 134 leads rod sled 136 (FIG. 5) during their travel through staple magazine 120. As staple sled 134 translates distally through staple magazine 120, rod sled 136 follows it after a predetermined time delay. Rod sled 136 is guided along its path by passage 135c of staple sled 134. Therefore, staple sled 134 ejects staple 110 and drives it against anvil member 142 to form a staple having a height of about 2.5 mm as discussed above. Once staple 110 has been driven into staple pocket 150, and before staple sled 134 passes staple ejector 132 (i.e. the delay between the sleds), sled 136 engages dimpling rod 138. As rod sled 136 translates distally with staple sled 134, it contacts dimpling rod 138 causing vertical motion thereof to engage backspan 116. Rod sled 136 drives dimpling rod 138 such that it forms a depression in the center of backspan 116 and further increasing the holding strength of the formed staple 110.

Figure 4:
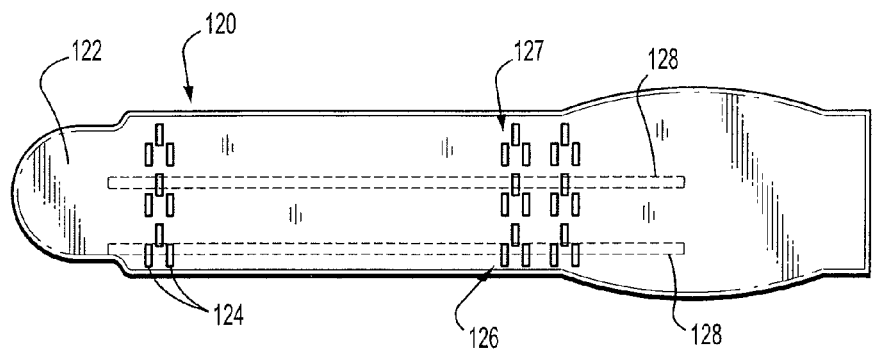
FIG. 4 is a top plan view of a staple magazine of the staple fastening assembly of FIG. 1.
Figure 5:
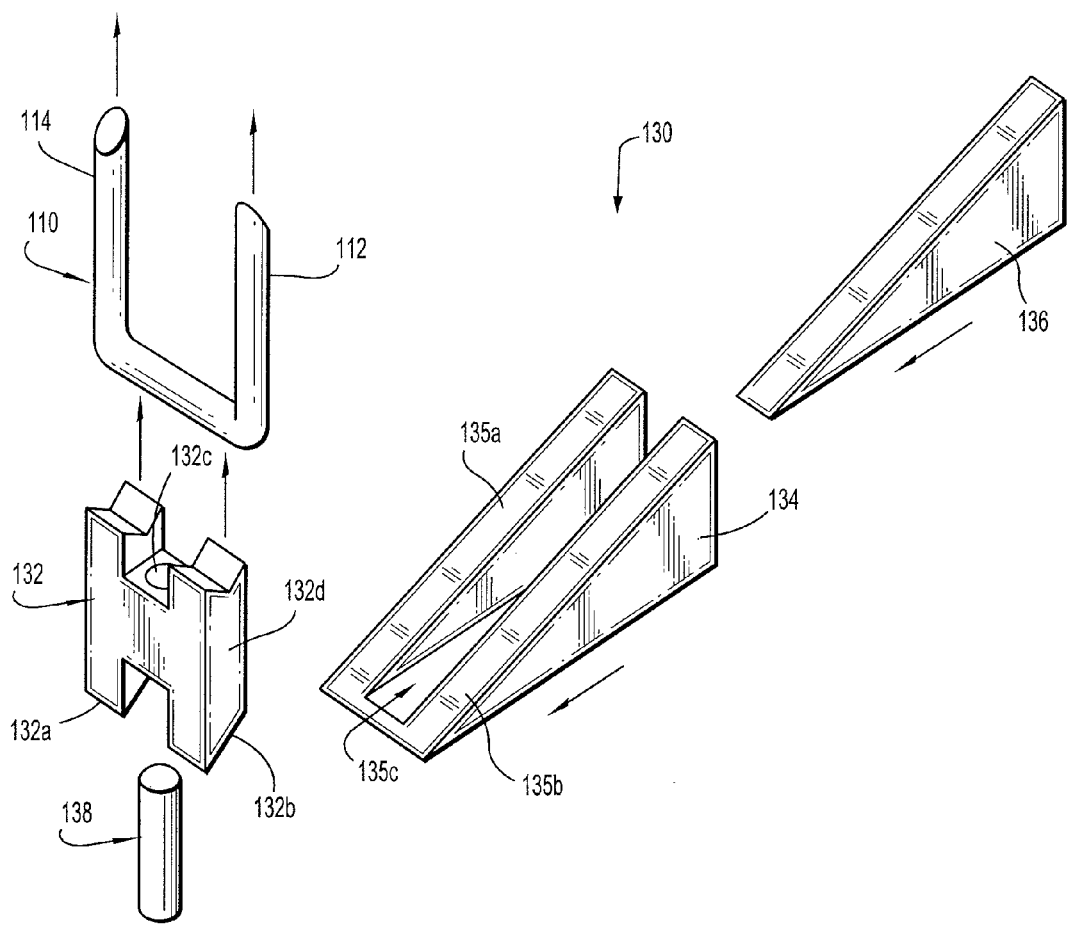
FIG. 5 is an exploded perspective view of a staple driving assembly showing the relationship among the several components.

As shown in FIG. 4, staple magazine 120 may have a plurality of rows 126 where retention slots 124 in each row 126 may be longitudinally offset from retention slots 124 in an adjacent row 126. Since retention slots 124 are longitudinally offset, staple crimping cams 134 are operatively arranged and synchronized to eject the first staple 110 from each row 126 and advancing sequentially towards a distal end of staple magazine 120 and sequentially ejecting staples 110 from each row 126.

As shown in FIGS. 1-3, second jaw 140 is spaced apart from first jaw 104 defining a tissue gap 102 therebetween. Second jaw 140 is moveable through a plurality of positions between an open position and a closed position. In one embodiment, first jaw 104 and second jaw 140 are substantially parallel to one another throughout the plurality of positions. During operation, discussed in detail below, of staple fastening assembly 100, second jaw 140 is moved towards first jaw 104 by jaw operating mechanism 160 that maintains a substantially parallel relationship between jaws 104 and 140.

Referring to FIG. 1, jaw operating mechanism 160 is disposed in a housing 170 and includes a cam 162, a cable 164, and a spring 166. Cam 162, cable 164, and spring 166 are operatively connected to one another. A proximal portion of second jaw 140 is disposed within housing 170 and secured thereto. In particular, spring 166 is operatively coupled to an approximating mechanism (not shown) of the stapling instrument by structures as are known in the art. The approximating mechanism causes spring 166 to move proximally. Since cable 164 is operatively connected to spring 166, this proximal movement of spring 166 results in proximal movement of cable 164 and counter-clockwise rotation of cam 162.

At least a portion of cam 162 contacts an outer surface 146 of second jaw 140 and it is self-locking in the counter-clockwise direction of rotation. Cam 162 has a centrally disposed orifice 163 for rotatably attaching it to housing 170. Although orifice 163 is substantially circular, cam 162 has a generally eccentric shape, particularly along an outside surface, such that counter-clockwise rotation of cam 162 causes at least a portion of cam 162 to maintain contact with outer surface 146 thereby urging second jaw 140 towards first jaw 104 during counter-clockwise rotation. After cam 162 has rotated a desired amount, it locks in position such that no clockwise rotation is possible (i.e. self-locking), but additional counter-clockwise rotation is possible. A release mechanism, as is known in the art, operatively couples jaw operating mechanism 160 to the surgical stapling instrument. After a complete actuation sequence, the release mechanism is actuated to unlock cam 162 and permit clockwise rotation of cam 162. Thusly, second jaw 140 is urged away from first jaw 104 by a biasing mechanism as is known in the art to separate the jaws and allow removal of the surgical stapling instrument.

In one embodiment, cam 162, cable 164, and spring 166 are selected such that tissue T is captured and maintained between jaws 104, 140 using a minimum amount of applied pressure. The advantageous combination of cam 162, cable 164, and spring 166 captures different thicknesses of tissue T (i.e. each tissue thickness corresponds to a particular tissue gap 102) while minimizing trauma to tissue T as jaws 104, 140 capture tissue T therebetween.

Figure 6A:
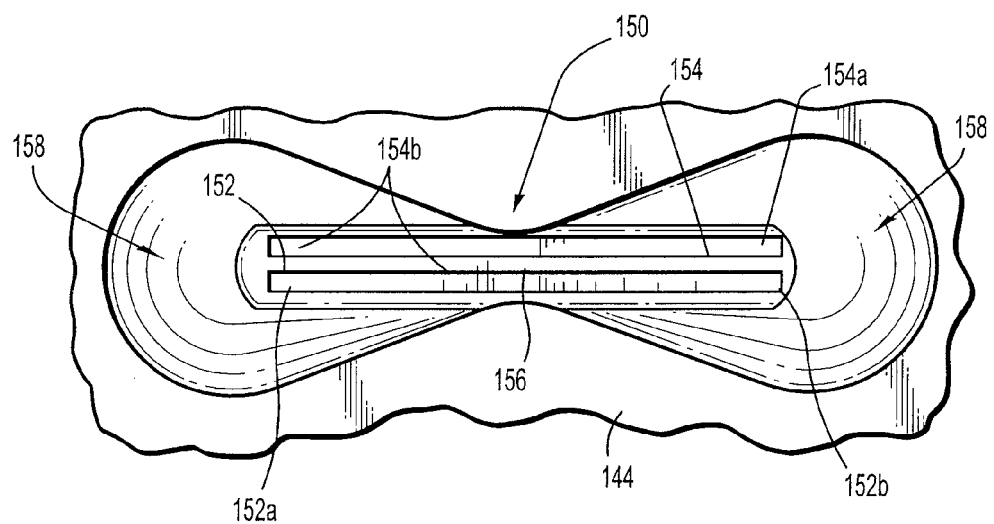
FIG. 6A is a top plan view of a staple pocket.
Figure 6:
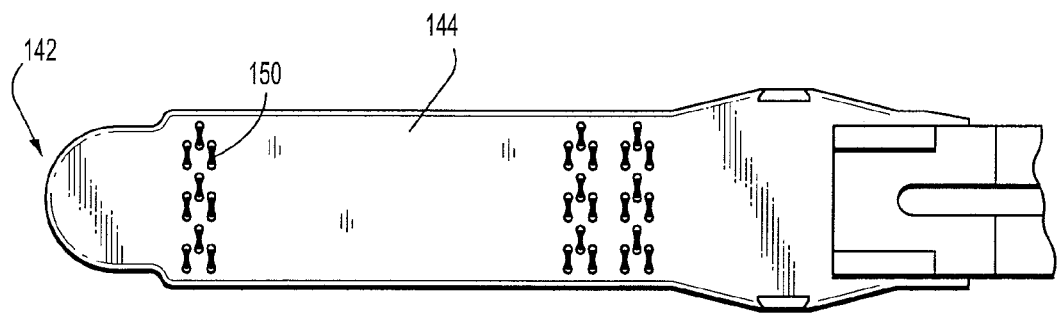
FIG. 6 is a bottom plan view of an anvil member.
Figure 7A:
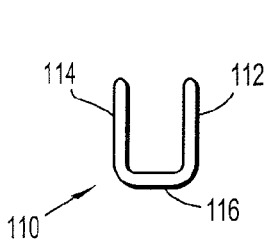
FIG. 7A is a side view of an unformed staple.

Referring now to FIG. 6, an anvil member 142 is illustrated. Anvil member 142 is generally elongate and includes a plurality of staple pockets 150 (see FIG. 6A) disposed on an second tissue contacting surface 144 where the number and arrangement of staple pockets 150 correspond to the number and arrangement of retention slots 124 in first tissue contacting surface 122. An example of a staple pocket is disclosed in U.S. Pat. No. 5,480,089 to Blewett. With reference now to FIG. 6A, each staple pocket 150 has a first staple leg forming groove 152 and a second staple leg forming groove 154 for forming respective legs 112, 114 of staple 110 (see FIG. 7A). Each staple forming groove 152, 154 is dimensioned to accommodate legs 112, 114 respectively.

Staple leg forming grooves 152 and 154 are symmetrical about an intermediate point 156. A substantially lemniscate (figure-eight shaped curve) channeling surface 158 is also formed in second tissue contacting surface 144 around a perimeter of staple pocket 150. Each channeling surface 158 forms an angle θ, with respect to a plane defined by second tissue contacting surface 144, wherein 0°<θ<90°. Each staple forming groove 152, 154 has a different slope than that of adjacent channeling surface 158. More particularly, each staple forming groove 152, 154 has a sloped end 152a, 154a to direct a corresponding staple leg 112, 114 towards a backspan 116 of staple 110. Sloped ends 152a, 154a are longitudinally opposed to one another.

During an actuation sequence, staple 110 is ejected from retention slot 124 and directed towards anvil member 142 thereby driving legs 112 and 114 through tissue T to enter staple forming grooves 152, 154 respectively. As staple 110 contacts staple pocket 150, staple forming grooves 152, 154 direct legs 112, 114 towards each other while maintaining lateral separation of legs 112, 114 so that they overlap one another as shown in FIG. 7F. In particular, with reference to FIGS. 7B-7D, during formation of staple 110, staple forming groove 152, in cooperation with channeling surface 158, directs leg 112 towards backspan 116 alongside and substantially parallel to an unformed portion of leg 114. Similarly, staple forming groove 154, in cooperation with channeling surface 158, directs leg 114 towards backspan 116 alongside and substantially parallel to an unformed portion of leg 112. The amount of parallel overlap between leg 112 and the unformed portion of leg 114 is a function of tissue gap 102. Similarly, the amount of parallel overlap between leg 114 and the unformed portion of leg 112 is also a function of tissue gap 102 that is controlled by the thickness of tissue T and operation of jaw operating mechanism 160.

Figure 7B:
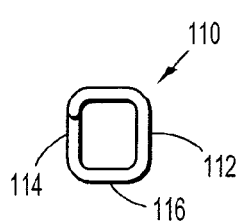
FIG. 7B is a side view of the staple of FIG. 7A formed to a first configuration in accordance with the present disclosure.
Figure 7C:
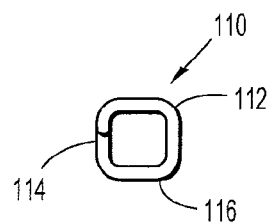
FIG. 7C is a side view of the staple of FIG. 7A formed to a second configuration in accordance with the present disclosure.
Figure 7D:
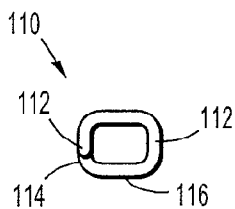
FIG. 7D is a side view of the staple of FIG. 7A formed to a third configuration in accordance with the present disclosure.
Figure 7E:
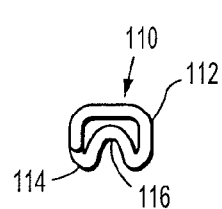
FIG. 7E is a side view of the staple of FIG. 7A formed to a fourth configuration in accordance with the present disclosure.
Figure 7F:
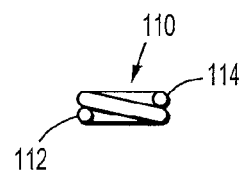
FIG. 7F is a plan view of the staple of FIG. 7B showing an overlap between first and second legs of the staple.
Figure 8A:
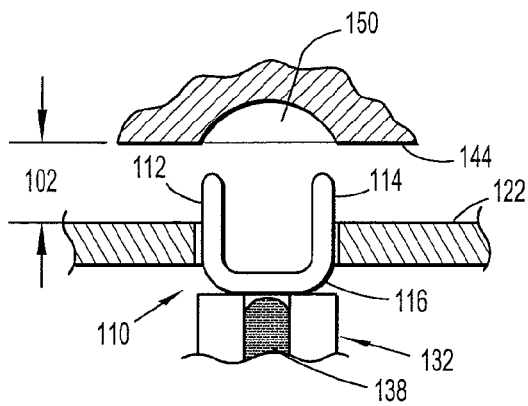
FIG. 8A is an enlarged side view of a staple pocket, an unformed staple, a staple sled, and a rod sled.
Figure 8B:
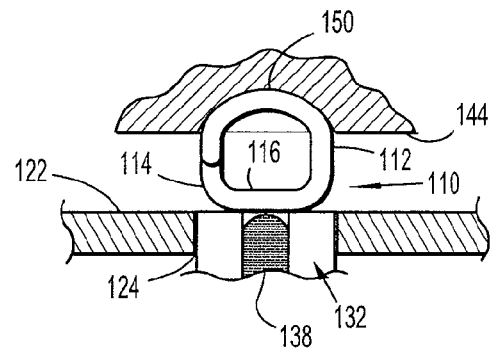
FIG. 8B is an enlarged side view of the components of FIG. 8A showing the staple formed into a first configuration.
Figure 8C:
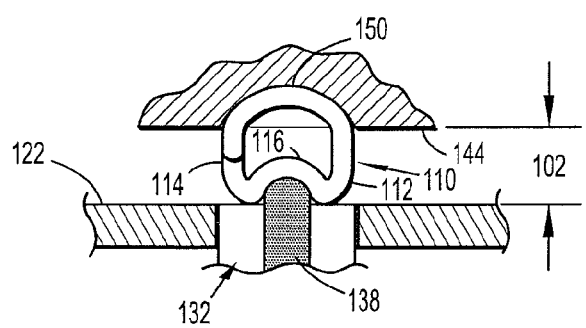
FIG. 8C is an enlarged side view of the components of FIG. 8B showing a backspan of the staple being dimpled by the dimpling rod.

Thusly, a larger tissue gap 102 results in a larger staple 110 height (e.g. about 4.8 mm as shown in FIG. 7B) while a smaller tissue gap 102 yields a smaller staple 110 height (e.g. about 2.5 mm as shown in FIG. 7D). In one embodiment, the actuation mechanism, in cooperation with staple magazine 120 and anvil member 142, forms staples 110 having a height of between about 4.8 mm (i.e. the open position of second jaw 140) and about 2.5 mm (i.e. the closed position of second jaw 140) as determined by the thickness of tissue T and tissue gap 102. It is to be understood that staples 110 may be formed having any height that is in the range of about 4.8 mm and about 2.5 mm as determined by the thickness of tissue T (an example is illustrated in FIG. 7C). In instances where tissue T thickness indicates a need for a smaller staple 110 height (i.e. less than about 2.5 mm or the dimpling position as seen in FIG. 7E), the actuation mechanism of the stapling instrument operates a second drive member that is operatively coupled to rod sled 136, as discussed hereinabove.

It will be understood that various modifications may be made to the embodiments disclosed herein. Therefore, the above description should not be construed as limiting, but merely as exemplifications of preferred embodiments. For example, the staple forming structure disclosed herein can be adapted and configured for use in EEA, TA, and endoscopic staplers with similar effect. Those skilled in the art will envision other modifications within the scope and spirit of the claims appended hereto.

What is claimed is:

1. A surgical apparatus comprising:
a housing including an actuating mechanism;
an elongate tubular member extending distally from the housing;
a staple fastening assembly located at a distal end of the elongate tubular member, the staple fastening assembly including a first jaw and a second jaw, the first jaw including a plurality of fasteners and a driving assembly, the second jaw including an anvil, the first jaw including at least one movable member disposed therein, the at least one movable member being selectively actuated for interacting with a portion of a surgical fastener;
a jaw driving assembly, the jaw driving assembly operatively coupled to the actuating mechanism such that actuation of the actuating mechanism moves one of the first and second jaws towards the other of the first and second jaws; and
at least one sled assembly, the sled assembly including first and second sleds, the first sled including a longitudinal passage therethrough for slidably receiving the second sled, wherein longitudinal translation of the first sled through the plurality of fasteners sequentially ejects the surgical fasteners and longitudinal translation of the second sled through the plurality of fasteners moves the at least one movable member towards the tissue contacting surface of the first jaw, the at least one movable member moving in a direction that is transverse to a longitudinal axis of the first jaw, and longitudinal translation of the first sled precedes longitudinal translation of the second sled defining a delay.

2. The surgical apparatus of claim 1, wherein the transverse movement of the at least one movable member contacts a portion of the surgical fastener.

3. The surgical apparatus of claim 1, wherein a portion of the second sled maintains contact with the passage of the first sled during longitudinal translation of the first and second sleds.

4. The surgical apparatus of claim 1, wherein each fastener interacts with the anvil to form a completed fastener, the completed fastener having a size that is proportional to a gap between tissue contacting surfaces of the first and second jaws, each of the movable members deforming the backspans of the corresponding fasteners when the gap is less than a predetermined amount.

5. A surgical apparatus comprising:
a housing including an actuating mechanism;
an elongate tubular member extending distally from the housing;
a staple fastening assembly located at a distal end of the elongate tubular member, the staple fastening assembly including first and second jaws, the first jaw including a fastener driving assembly operatively associated with the actuating mechanism, the fastener driving assembly having first and second sleds, the first sled having a longitudinal passage therethrough for slidably receiving the second sled, the second jaw including an anvil;
a plurality of fasteners and a corresponding number of ejector assemblies disposed in the first jaw, each ejector assembly including a fastener ejector and a movable member, wherein the first sled translates distally in response to actuation of the fastener driving assembly and the second sled remains stationary; and
a jaw driving assembly operatively coupled to the actuating mechanism.

6. The surgical apparatus of claim 5, wherein a gap is defined between tissue contacting surfaces of the first and second jaws, the gap being proportional to tissue captured between the first and second jaws.

7. The surgical apparatus of claim 6, wherein distal movement of the first sled causes movement of the ejectors in a direction that is transverse to a longitudinal axis of the first jaw, thereby driving the fasteners towards the anvil.

8. The surgical apparatus of claim 7, wherein each fastener interacts with the anvil to form a completed fastener, the completed fastener having a size that is proportional to the gap.

9. The surgical apparatus of claim 7, wherein the second sled translates distally through the plurality of fasteners, the second sled engaging the movable members and driving the movable members in a direction that is transverse to the longitudinal axis of the first jaw.

10. The surgical apparatus of claim 9, wherein each of the movable members contacts a backspan of its corresponding fastener.

11. The surgical apparatus of claim 10, wherein each fastener interacts with the anvil to form a completed fastener, the completed fastener having a size that is proportional to a gap between tissue contacting surfaces of the first and second jaws, each of the movable members deforming the backspans of the corresponding fasteners when the gap is less than a predetermined amount.

* * * * *